United States Patent [19]

Niznick

[11] Patent Number: 5,061,181

[45] Date of Patent: Oct. 29, 1991

[54] DENTAL IMPLANT INCLUDING PLURAL ANCHORING MEANS

[75] Inventor: Gerald A. Niznick, Encino, Calif.

[73] Assignee: Core-Vent Corporation, Encino, Calif.

[21] Appl. No.: 391,201

[22] Filed: Aug. 11, 1989

Related U.S. Application Data

[63] Continuation-in-part of Ser. No. 1,807, Jan. 6, 1987.

[51] Int. Cl.$^5$ ............................................. A61C 8/00
[52] U.S. Cl. .................................................... 433/174
[58] Field of Search ................ 433/173, 174, 175, 176

[56] References Cited

U.S. PATENT DOCUMENTS

| | | | |
|---|---|---|---|
| 3,499,222 | 3/1970 | Linkow et al. | 433/174 |
| 3,919,774 | 11/1975 | Fishman | 433/224 |
| 4,324,550 | 4/1982 | Reuther et al. | 433/174 |
| 4,334,865 | 6/1982 | Borle | 433/221 |
| 4,468,200 | 8/1984 | Münch | 433/174 |

FOREIGN PATENT DOCUMENTS

| | | |
|---|---|---|
| 2063680 | 6/1981 | United Kingdom . |
| 2112683 | 7/1983 | United Kingdom . |
| 2117641 | 10/1983 | United Kingdom . |
| 2199502 | 7/1988 | United Kingdom . |
| 8504321 | 10/1985 | World Int. Prop. O. . |

*Primary Examiner*—Gene Mancene
*Assistant Examiner*—Michael Lynch

[57] ABSTRACT

A dental implant anchor includes a body portion having a first external wall portion carrying one or more circumferential projections separated by circumferential grooves and, below, a second external wall portion carrying threads. In some forms, the anchor also includes one or more longitudinally-oriented grooves on its exterior wall. The grooves extend across, and through the circumferential projections. The implant can include a head portion with a smooth external wall; a through-hole and an apical hole passing through the bottom of the implant; and internal structure for engaging a tool for inserting the implant in a passage formed in bone tissue. This internal structure can be in a top portion, or in an internal passage in the body portion of the implant. The method for forming a passage in bone tissue to receive the implant includes forming a passage having a base with a diameter suited to self-tapping of the threaded part of the implant, and, above the base, a larger-diameter section to engage frictionally the circumferential projections. A drill for forming such a passage in one step includes two such drilling portions that simultaneously form a two-diameter passage.

18 Claims, 5 Drawing Sheets

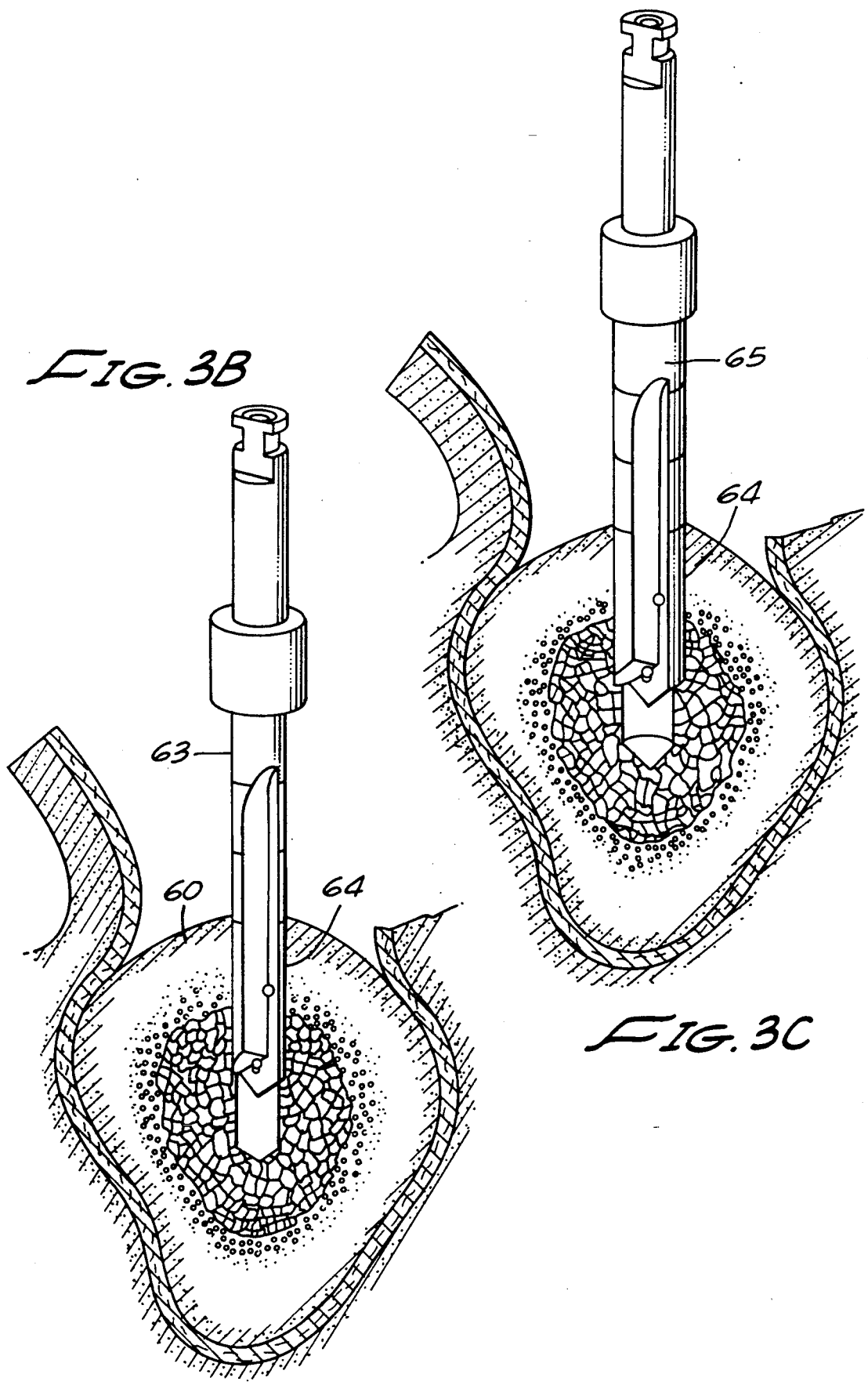

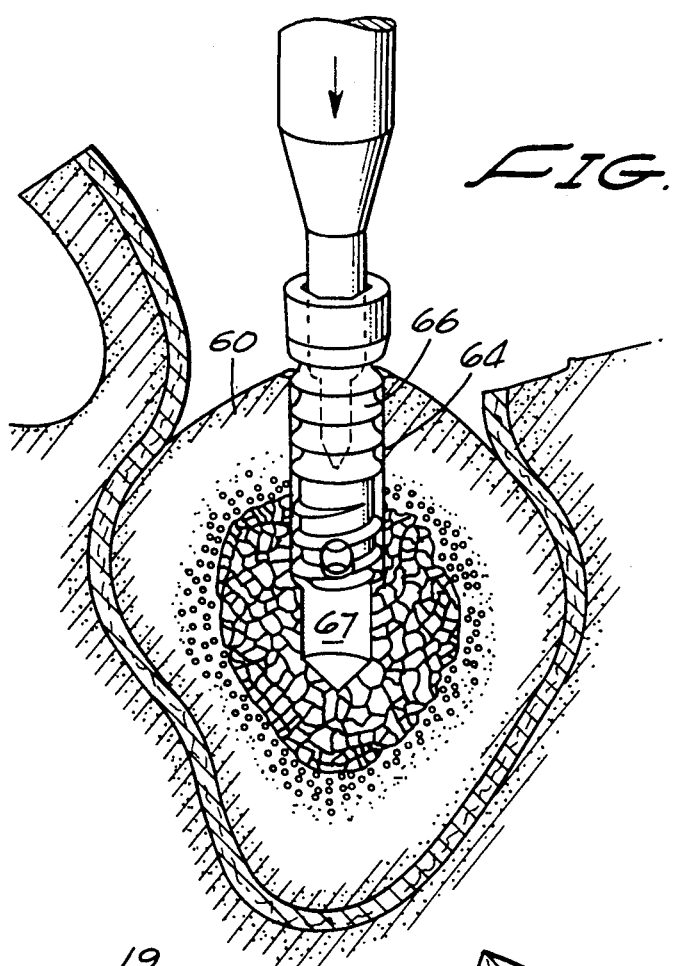
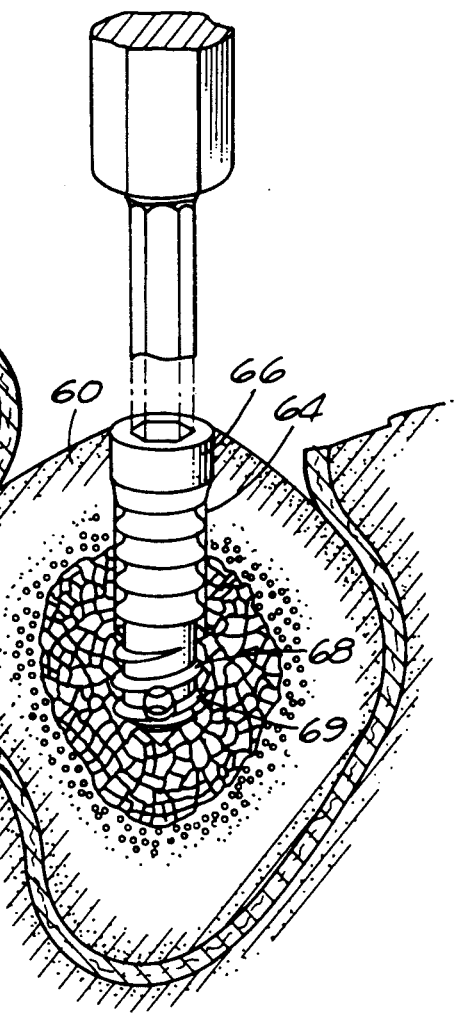
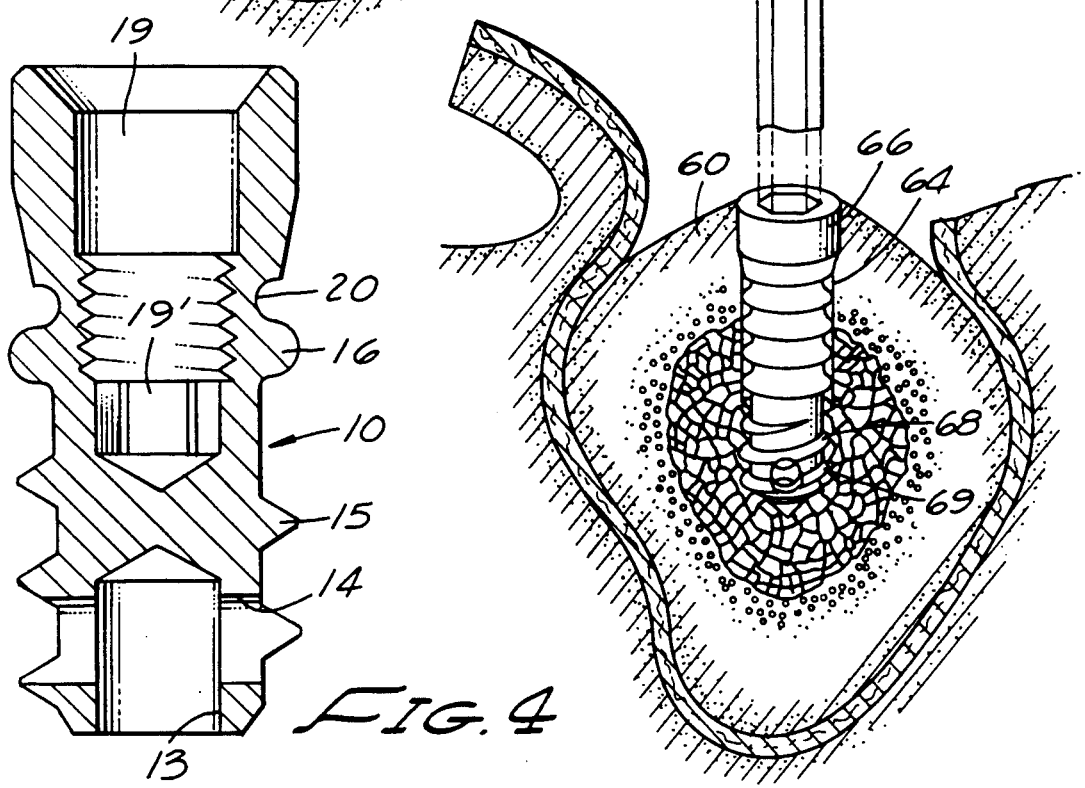

DENTAL IMPLANT INCLUDING PLURAL ANCHORING MEANS

This application is a continuation-in-part of U.S. patent application Ser. No. 07/001,807, filed Jan. 8, 1987, and entitled, "Dental Implant Including Plural Anchoring Means."

This invention relates to dental implant anchoring means having, on its outer wall, a plurality of anchoring means including an outer wall portion carrying circumferential or partially circumferential projections and an outer wall portion carrying threads. The outer wall portion also includes, in preferred embodiments, two or more longitudinally-oriented grooves. These grooves intersect the circumferential projections, preferably at right angles. In preferred embodiments, each of these grooves extend through all of the circumferential projections on the outer wall portion. Preferably, these grooves are of sufficient width and depth to promote bone growth into them of sufficient quantity and quality to minimize rotation of the implant when inserted into an opening in bone tissue. Preferably, these grooves are about 0.25 mm to about 1.5 mm in depth and in width.

This anchoring means preferably includes a body portion and a top portion with the body portion carrying the plurality of anchoring means on its outer wall. In these preferred embodiments, the top portion has a smooth external wall that tapers upwardly and outwardly from the body portion to a diameter that is slightly larger than the diameter of the body portion. The top portion is sufficiently large in diameter to insure that the top portion fits snugly within, and tightly seals, by frictional forces, in the top of a passage formed in bone tissue to receive the dental implant anchoring means. Alternatively, the top portion can be of substantially the same diameter as, or even of smaller diameter than the body portion of the implant.

The dental implant anchoring means preferably includes, at its distal end, a through hole extending from one side of the body portion to the other to permit bone and associated tissue to grow through this opening. The distal end preferably also includes a passage at the bottom of the body portion that extends upwardly inside the body portion a distance sufficient to permit blood and other tissue to pass upwardly, out the through-hole and up the longitudinally-oriented grooves, thus allowing the anchor to seat at the bottom of the passage formed in bone tissue to receive the implant. Preferably, this upwardly-extending passage is less than about one-third the length of the body portion.

The implant has an internal passage extending downwardly from the top of the implant, and internal means for engaging and inserting the implant into a passage formed in bone tissue to receive the implant. The internal implant-engaging means permits insertion of the implant in a passage formed in the bone tissue of a subject without countersinking the upper surface of the bone tissue, where the top portion of the implant fits upon insertion of the implant into such a passage. This internal means is, preferably, a wrench-engaging surface. In preferred embodiments, where the body portion is joined to a top portion having an unthreaded, smooth exterior wall, the internal means for implant insertion is inside this top portion. Alternatively, this internal means can be inside the body portion in an internal passage. Preferably, the top portion has a hex nut configuration on its inner wall surfaces for receiving a hex wrench, and has a cylindrically-shaped, smooth outer wall. Alternatively, the hex nut configuration can be within, and at or near the base of the passage inside the body portion, or formed within threads on the wall of this passage.

In embodiments that include a top portion, the top portion is open, and can be chamfered at its upper end, and is preferably axially aligned with an internal passage in the body portion. The passage can be threaded or unthreaded. This chamfered surface permits frictional locking with any adaptor or other insert fitted into the opening. The chamfered surface is preferably of sufficient size and depth to afford lateral stability to any adaptor or other insert fitted into the opening in the head portion, and forms a smooth, easily-cleaned margin with complementary adaptors placed in the top portion of the implant.

The anchoring means is preferably made of titanium or a titanium alloy containing 6% by weight of aluminum and 4% by weight of vanadium; preferably has an outside thread diameter in the range of about 3 to about 4.25 millimeters; an inside thread diameter in the range of about 2.25 to about 3.5 millimeters; and preferably has projections with an outside diameter that is substantially the same as, or about 0.25 millimeter larger than the thread diameter. The anchoring means preferably has a length in the range of about 5 to 20 millimeters.

The implant anchors of this invention are adapted for insertion in specially-formed passages in bone tissue. Preferably, the method of forming such a passage includes forming a passage in the bone tissue having an upper portion with a length and a diameter suitable for engaging the flutes or circumferential projections on the anchor by friction, and including, at the base of the passage, a smaller-diameter portion adapted to engage the self-tapping threads at the bottom of the implant. The smaller-diameter portion at the base of the opening can be formed using a first drill having a cross-section appropriate to form a passage of this diameter and with length that is about the same as the length of the implant to be inserted. Thereafter, the upper portion of the passage can be enlarged by a drill of appropriate diameter to accommodate the fluted part of the body portion of the implant. Alternatively, the smaller diameter and larger diameter portions of the passage can be formed simultaneously using a drill having, at its end, a portion of a diameter appropriate for forming the smaller diameter portion of the passage, and an upper portion of larger diameter suitable for forming the upper portion of the passage. The implant anchor is tapped into the passage so formed until the bottom of the threaded portion reaches the top of the portion of smaller diameter at the base of the passage. Then, using an insertion tool to engage the wrench-engaging surface inside the implant, the implant can be screwed into the smaller-diameter part of the passage until the threaded part of the implant reaches the bottom of the passage.

This invention can better be understood by reference to the drawings, in which:

FIGS. 3A-3E show the preferred five-step method for inserting the new dental implant anchors in the bone tissue of a subject;

FIG. 4 shows an elevational view, in cross-section, of a third embodiment of a new dental implant anchor;

Figure 1:
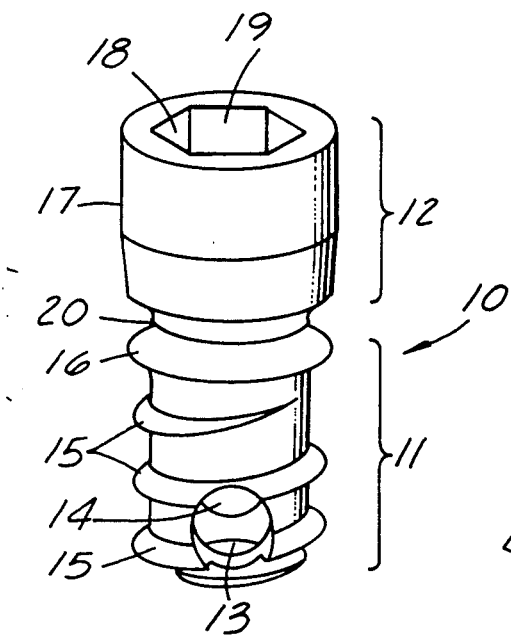
FIG. 1 is a perspective view of a first embodiment of the new dental implant anchor.

FIG. 1 shows a first embodiment of the new dental implant anchor generally designated 10. Anchor 10 includes body portion 11 joined to, and surmounted by top portion 12. Body portion 11 includes circumferential projection 16, called a flute, spaced from top portion 12 by circumferential groove 20 on body portion 11. Below flute 16 on body portion 11 are threads 15. At the bottom of body portion 11 is through-hole 14 which passes axially through body portion 11, and apical hole 13, formed at the bottom of implant 10, and extending upwardly inside body portion 11 beyond through-hole 14.

Top portion 12 is joined to, and surmounts body portion 11. Top portion 12 has a sidewall 17 that tapers upwardly and outwardly from the plane, near groove 20, where body portion 11 joins top portion 12.

Atop top portion 12 is opening 19 with wrench-engaging surface 18 on the inner wall of top portion 12. This wrench-engaging surface 18 permits threading of implant 10 into a passage formed in bone tissue by means of a tool that fits inside implant 10, obviating the need for any insertion tool-engaging means on the outside surface of implant 10. Opening 19 can, in some embodiments, be in registration with a shaft formed inside body portion 11, and the wrench-engaging surface 18 can, in such embodiments, be at or near the base of the shaft internal to implant 10.

Figure 2:
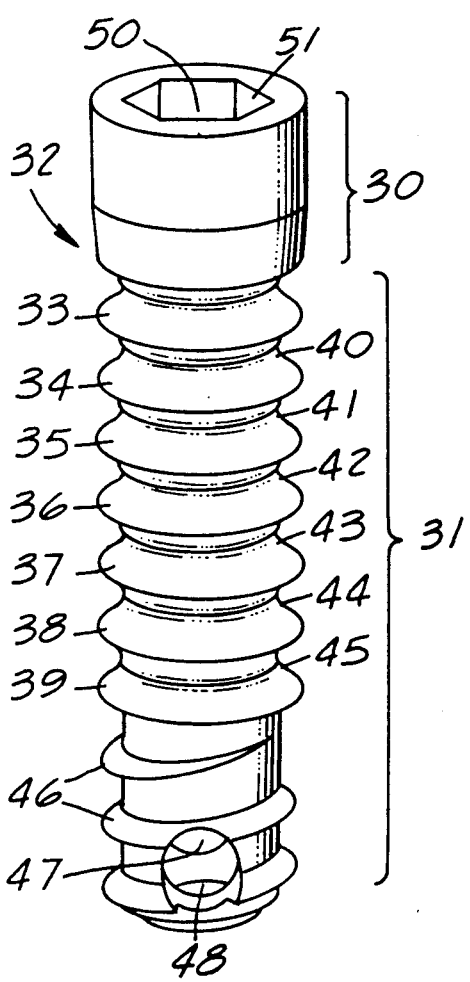
FIG. 2 is a perspective view of a second embodiment of the new dental implant anchor.

FIG. 2 shows a second embodiment of the new implant, generally designated 32, that includes head portion 30 and body portion 31. Body portion 31 includes an external wall portion carrying a plurality of circumferential projections 33, 34, 35, 36, 37, 38 and 39. These projections are in planes parallel to one another and are separated from one another by grooves 40, 41, 42, 43, 44 and 45. Below circumferential flutes 33-39 is another wall portion carrying threads 46. The flutes facilitate seating the implant frictionally in a passage formed in bone tissue by tapping the implant into such a passage. Threads 46 at the bottom of body portion 31 permit the implant to be screwed into the bottom of such a passage. Thus, the implant can be held in place in such a passage by both the flutes and the threads, or by either one alone if the other fails. Implant 32 also includes through hole 47 and apical opening 48 which correspond to, and perform the same functions as openings 13 and 14, respectively, in FIG. 1.

Top portion 30 includes opening 50 and wrench-engaging surface 51, which are identical to, and function the same as opening 19 in wrench-engaging surface 18, respectively, in FIG. 1. As in FIG. 1, the opening 50 may be in registration with a shaft internal to body portion 31, and the wrench-engaging surface 51 can lie inside the shaft instead of inside head portion 30.

FIG. 4 shows a third embodiment of the new dental implant anchoring means. In most respects, this implant is identical to the implant shown in FIG. 1, except that the internal wrench-engaging surface 19' lies at the bottom of the internal passage inside the implant instead of on the internal surfaces of the top portion of the implant. While FIG. 4 shows the internal passage, below the top portion, to be partially threaded to receive and engage with threaded or unthreaded inserts such as dental prostheses, the threading is not mandatory, and the walls of the internal passage can, in alternative embodiments, be smooth instead of threaded, or partly threaded or partly smooth.

Figure 3A:
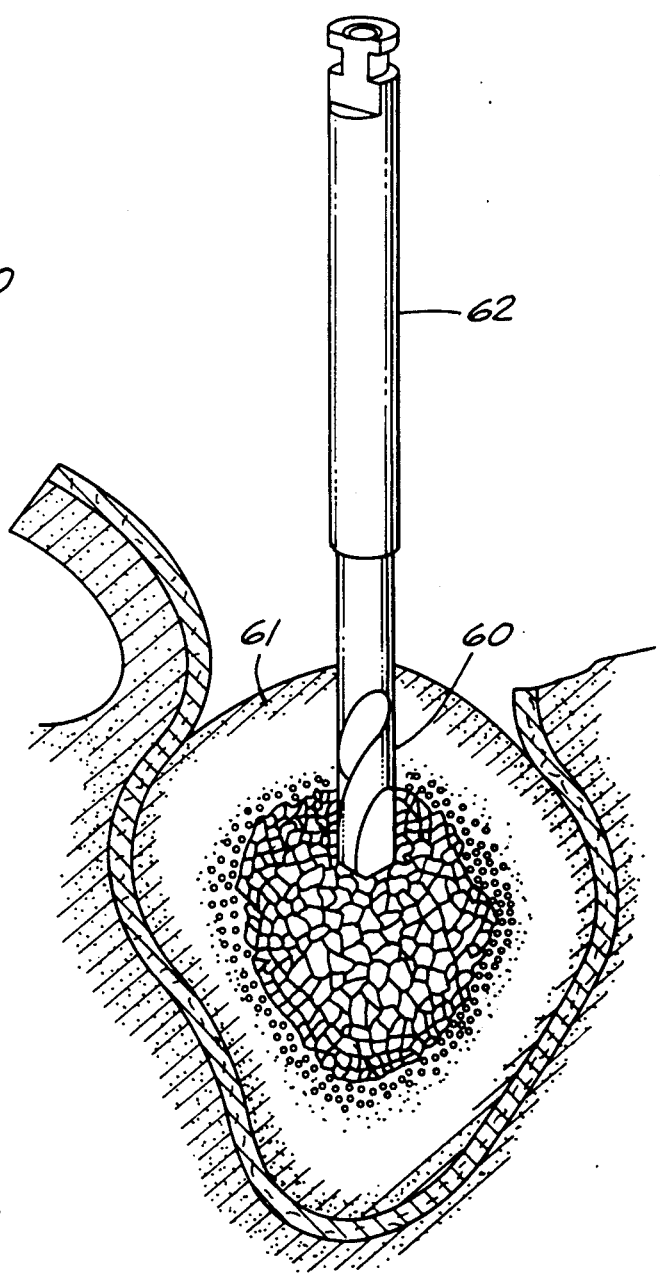

FIGS. 3A-3E show the preferred five-step method for inserting the new implants into bone tissue. FIG. 3A shows the formation of a pilot passage 60 in bone tissue 61 using a small-diameter pilot drill 62, say a drill having a diameter of about 2 millimeters. FIG. 3B shows using a spade drill 63 of slightly larger diameter than the pilot drill 62, say a diameter of 2.5 millimeters, to form a passage 64 in bone tissue 60 having a length substantially the same as the length of the implant to be inserted, and a diameter substantially the same as the diameter of the threaded, lower portion of the implant. FIG. 3C shows using a spade drill 65 of slightly larger diameter than the first spade drill 63, say approximately 3.2 millimeters, to enlarge the upper portion of the passage 64 formed in bone tissue in FIG. 3B to a diameter substantially the same as the diameter of the projections or flutes on the outer wall of the body portion above the threaded portion on the same wall. FIG. 3D shows inserting implant 66 into the passage formed in FIG. 3C by tapping implant 66 downwardly until the bottom of implant 66 reaches the top of smaller-diameter portion 67 of passage 64. FIG. 3E shows the final step of inserting implant 66 into passage 64 formed in bone tissue by ratcheting self-tapping threads 68 at the bottom of implant 66 into smaller diameter portion 69 of passage 64 formed in bone tissue 60.

Figure 5:
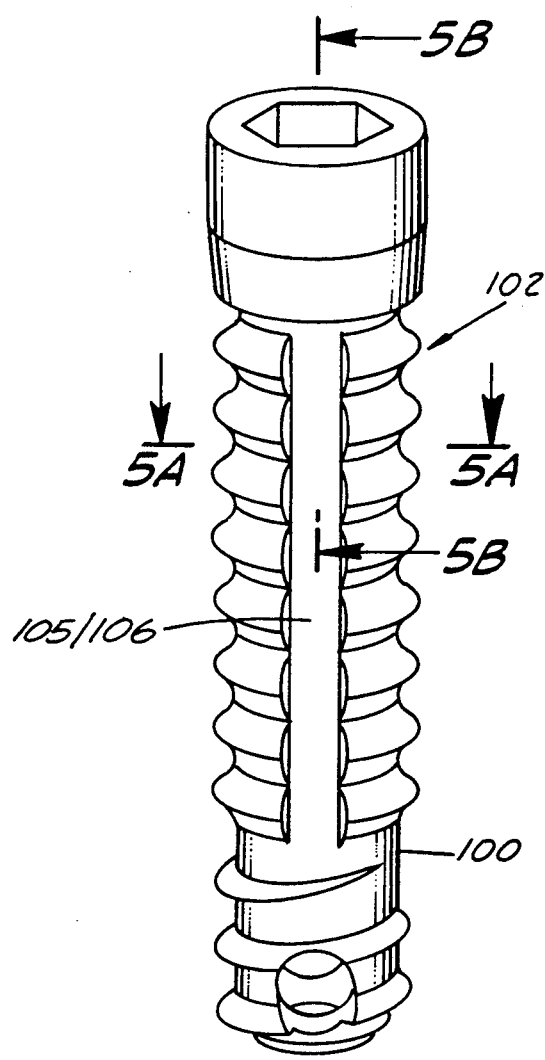
FIGS. 5 and 6 show fourth and fifth embodiments of the new dental implant anchoring means.
Figure 5A:
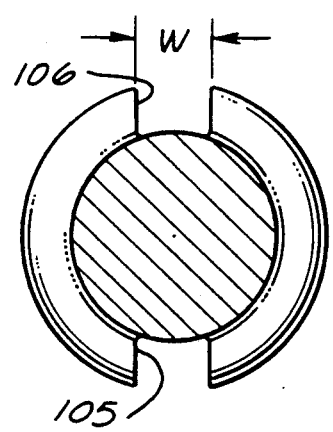
FIG. 5A is a top plan cross-sectional view, taken on line 5A—5A in FIG. 5, showing the width of the longitudinal grooves on the exterior wall of the fourth embodiment shown in FIG. 5.
Figure 6:
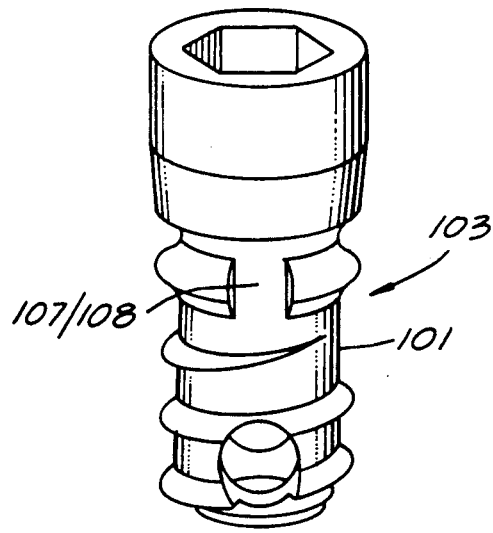
Figure 5B:
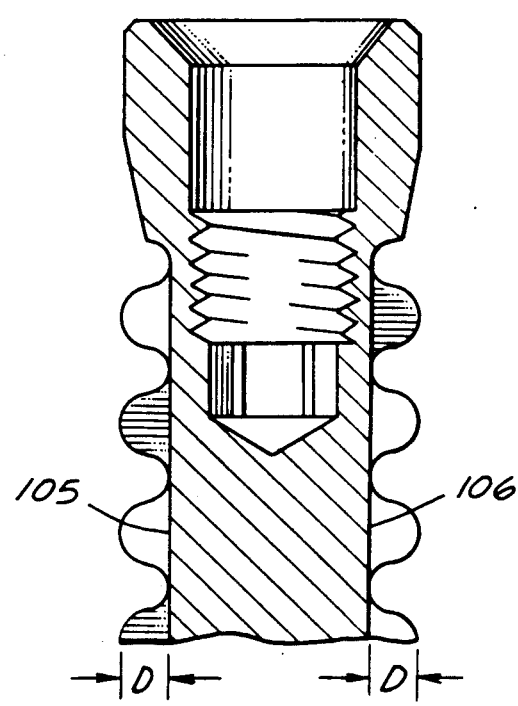
FIG. 5B is a longitudinal cross-sectional view, taken on line 5B—5B of FIG. 5, showing the depth of the longitudinal grooves shown in FIG. 5A.

FIGS. 5 and 6 show fourth and fifth embodiments of the new dental implant anchoring means. In most respects, the implants of FIGS. 5 and 6 are identical to those shown in FIGS. 2 and 4. However, the outer wall surfaces 100 (FIG. 5) and 101 (FIG. 6) of each of these implants 102 and 103 has two longitudinally-extending grooves 105/106 (FIG. 5) and 107/108 (FIG. 6) that are diametrically disposed on opposite sides of the other wall and that extend from just below the base of the top portion entirely through the circumferential projections from top to bottom. These grooves interrupt, and extend across and through these circumferential projections on each side of the implant. These grooves are of sufficient depth and width, here about 0.25 mm to about 1.5 mm in depth (see FIG. 5B) and in width (see FIG. 5A), to insure that bone tissue will grow into these grooves enhancing the anchoring of the implants to the bone tissue.

Figure 7:
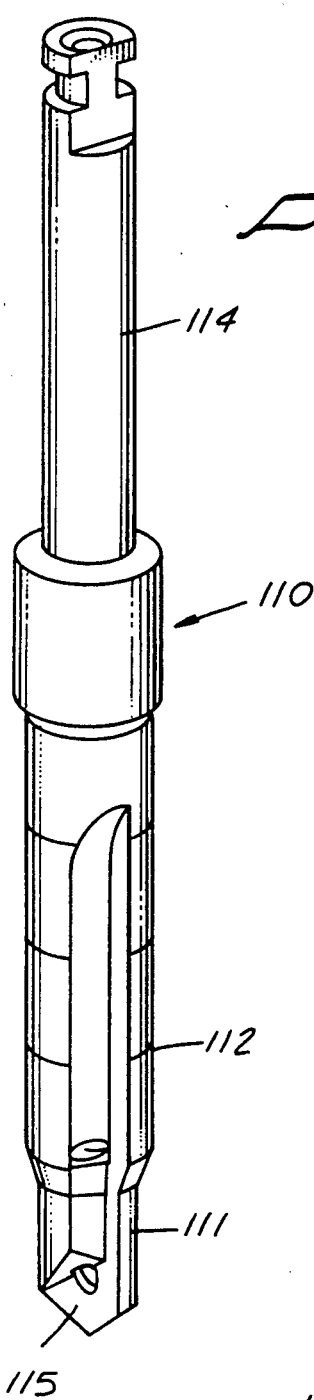
FIG. 7 shows a perspective view of a new spade drill adapted for forming an opening in bone tissue for receiving the dental implant anchors of this invention.
Figure 8:
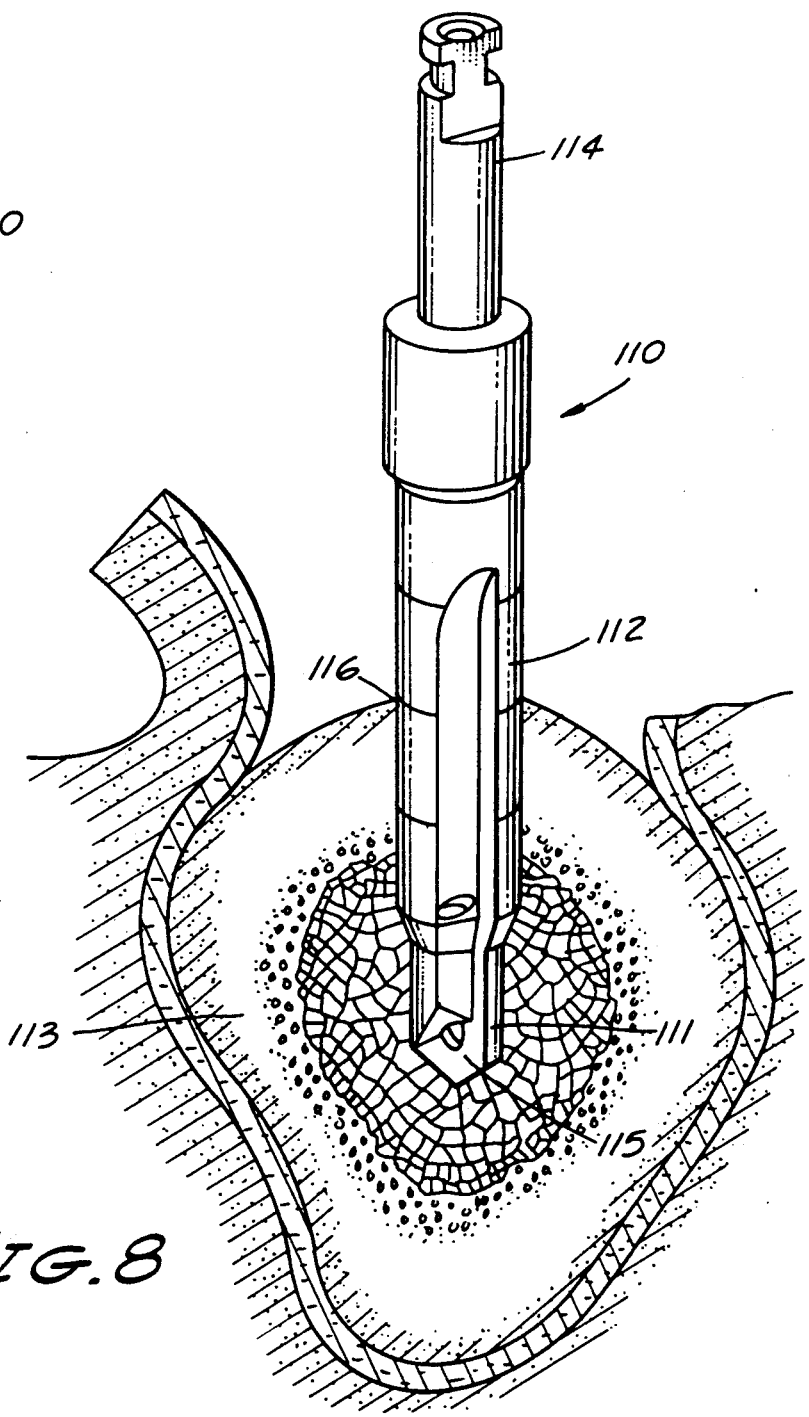
FIG. 8 shows penetration of the drill of FIG. 7 into bone tissue to form such an opening.

FIG. 7 shows a spade drill 110 having a first portion 111 and a second portion 112. Spade drill 110 is adapted to form a generally cylindrically-shaped passage in bone tissue with a portion having a first diameter and a portion having a second larger diameter. The first passage portion, of smaller diameter, is formed by first drill portion 111; the second passage portion, of larger diameter, is formed by second drill portion 112. Spade drill 110 is adapted to form such a cylindrical-shaped passage in bone tissue with two portions of differing diameters in a single drilling operation. See FIG. 7, where drill 110 penetrates into bone tissue 113 under power provided by a drilling apparatus (not shown) attached to stem 114 of drill 110. Drill 110 also includes a spade-shaped portion 115 which tends to push bone tissue upwardly toward the crest of bone 116 as drill 110 penetrates bone 116 (see FIG. 7).

The implants of this invention have several advantages. First, the rounded flutes provide a surface adapted to receive coatings of material such as hydroxyl apatite or other bone substitute materials. The flutes also provide irregular surfaces for better distribution of stresses on the implant from dental prostheses attached thereto. The openings and the longitudinally-oriented grooves permit blood and other tissue at the bottom of a passage formed in bone tissue to receive these implants to pass upwardly so that the implants can seat fully at the bottom of such a passage. The upwardly, outwardly tapered head portion insures that the implant, when inserted in a passage formed in bone tissue of sufficient depth to receive the entire implant, seats firmly and snugly at the mouth of the passage.

What is claimed is:

1. A substantially cylindrical dental implant anchoring means comprising a substantially cylindrical body portion adapted to fit in a passage formed in jawbone tissue, said body portion having an external wall portion carrying at least two circumferential or partially circumferential projections, each of said projections having a size and shape adapted to engage the walls of said passage substantially exclusively frictionally, each of said projections having a cross-section sufficiently large to engage frictionally the sidewalls of said passage, and to hold said anchoring means inside said passage immediately upon insertion of said dental implant anchoring means into said passage, each of said circumferential projections having a groove on each side of the projection to facilitate growth of bone tissue into said grooves to promote anchoring of said dental implant in said passage, and, below at least said two projections, an external wall portion carrying thread means adapted to screw into the end of said passage, said thread means having its axis at an oblique angle to the longitudinal axis of said substantially cylindrical dental implant;

said anchoring means further comprising:

at least two longitudinally-extending grooves passing through and interrupting each of said circumferential projections, each of said grooves being of sufficient depth and width to ensure bone growth into said grooves when said anchoring means is seated inside said passage.

2. The dental implant anchoring means of claim 1 further comprising, above said body portion, a top portion having a smooth external wall, said top portion slanting outwardly and upwardly from a plane through said portion where said body portion joins said top portion.

3. The dental implant anchoring means of claim 2 further comprising means internal to said implant for engaging means for inserting said implant in said passage.

4. The dental implant anchoring means of claim 3 further comprising a through-hole passing laterally through said body portion near the bottom of said body portion.

5. The dental implant anchoring means of claim 3 wherein said implant includes two of said longitudinally-extending grooves, each of said grooves intersecting said circumferential projections at substantially right angles, each of said two grooves lying on opposite sides of the circumference of said external wall portion.

6. The dental implant anchoring means of claim 3 wherein each of said projections has its circumferential axis substantially normal to the longitudinal axis of said substantially cylindrical dental implant.

7. The dental implant anchoring means of claim 4 further comprising an apical hole in the body portion of said implant extending upwardly inside said body portion beyond said through-hole.

8. The dental implant anchoring means of claim 4 wherein said implant includes two of said longitudinally-extending grooves, each of said grooves intersecting said circumferential projections at substantially right angles, each of said two grooves lying on opposite sides of the circumference of said external wall portion.

9. The dental implant anchoring means of claim 4 wherein each of said projections has its circumferential axis substantially normal to the longitudinal axis of said substantially cylindrical dental implant.

10. The dental implant anchoring means of claim 7 wherein said plant includes two of said longitudinally-extending grooves, each of said grooves intersecting said circumferential projections at substantially right angles, each of said two grooves lying on opposite sides of the circumference of said external wall portion.

11. The dental implant anchoring means of claim 7 wherein each of said projections has its circumferential axis substantially normal to the longitudinal axis of said substantially cylindrical dental implant.

12. The dental implant anchoring means of claim 2 wherein said implant includes two of said longitudinally-extending grooves, each of said grooves intersecting said circumferential projections at substantially right angles, each of said two grooves lying on opposite sides of the circumference of said external wall portion.

13. The dental implant anchoring means of claim 2 wherein each of said projections has its circumferential axis substantially normal to the longitudinal axis of said substantially cylindrical dental implant.

14. The dental implant anchoring means of claim 1 wherein said implant includes two of said longitudinally-extending grooves, each of said grooves intersecting said circumferential projections at substantially right angles, each of said two grooves lying on opposite sides of the circumference of said external wall portion.

15. The dental implant anchoring means of claim 14 wherein each of said projections has its circumferential axis substantially normal to the longitudinal axis of said substantially cylindrical dental implant.

16. The dental implant anchoring means of claim 1 wherein each of said projections has its cirucmferential axis substantially normal to the longitudinal axis of said substantially cylindrical dental implant.

17. A method for inserting a dental implant including plural anchoring means in a passage formed in jawbone tissue to receive said dental implant anchoring means comprising forming a passage in bone tissue having a bottom portion of a first diameter and, atop said bottom portion, a second portion having a larger diameter; inserting into said passage a dental implant anchoring means comprising a body portion adapted to fit in a passage formed in bone tissue, said bone portion having an external wall portion carrying at least two projections, each of said projections having a size and shape adapted to engage the walls of said passage substantially exclusively frictionally, at least two longitudinally-extending grooves passing through and interrupting each of said circumferential projections, each of said grooves being of sufficient depth and width to ensure bone growth into said grooves when said anchoring means is seated inside said passage, said projections having a cross-section sufficiently large to engage frictionally the sidewalls of said passage, and to hold said anchoring means inside said passage immediately upon insertion of said dental implant anchoring means into said passage, and, below at least said one projection, an external wall portion carrying thread means adapted to screw into the end of said passage, said thread means having its axis at an oblique angle to the longitudinal axis of said substantially cylindrical dental implant, and tapping said implant anchoring means into said passage sufficiently far that said external wall portion carrying thread means reaches the top of the portion of the passage having said first diameter; and then screwing said dental implant anchoring means into said passage until said external wall portion carrying threads is threaded into the smaller diameter portion of said passage.

18. The method of claim 17 further comprising forming said passage in two steps, utilizing two separate passage-forming means, the first of said passage-forming means having a diameter appropriate for forming the bottom portion of the passage, and the second having a larger diameter appropriate for forming the upper portion of said passage.

* * * * *